US010825563B2

(12) United States Patent
Gibby et al.

(10) Patent No.: US 10,825,563 B2
(45) Date of Patent: Nov. 3, 2020

(54) ALIGNING IMAGE DATA OF A PATIENT WITH ACTUAL VIEWS OF THE PATIENT USING AN OPTICAL CODE AFFIXED TO THE PATIENT

(71) Applicant: Novarad Corporation, American Fork, UT (US)

(72) Inventors: Wendell Arlen Gibby, Mapleton, UT (US); Steven Cvetko, Draper, UT (US); Jacob Troy Gibby, Arlington, VA (US)

(73) Assignee: NOVARAD CORPORATION, American Fork, UT (US)

( * ) Notice: Subject to any disclaimer, the term of this patent is extended or adjusted under 35 U.S.C. 154(b) by 306 days.

(21) Appl. No.: 15/979,283

(22) Filed: May 14, 2018

(65) Prior Publication Data

US 2019/0348169 A1 Nov. 14, 2019

(51) Int. Cl.
*G16H 30/20* (2018.01)
*G06K 7/14* (2006.01)
*G06K 19/06* (2006.01)

(52) U.S. Cl.
CPC ........... *G16H 30/20* (2018.01); *G06K 7/1417* (2013.01); *G06K 19/06037* (2013.01)

(58) Field of Classification Search
CPC ... G06F 3/011; G03G 15/04027; A61B 5/055; G06T 15/503; G06Q 10/063118; G06Q 50/22–24
See application file for complete search history.

(56) References Cited

U.S. PATENT DOCUMENTS

| 5,075,787 | A | * | 12/1991 | Shaughnessy ... G03G 15/04027 358/448 |
| 6,675,040 | B1 | | 1/2004 | Cosman |
| 9,892,564 | B1 | | 2/2018 | Cvetko et al. |
| 10,078,917 | B1 | * | 9/2018 | Gaeta ................... G02B 27/017 |
| 2013/0267838 | A1 | | 10/2013 | Fronk et al. |

(Continued)

OTHER PUBLICATIONS

United States Patent and Trademark Office; International Search Report and Written Opinion issued in Application No. PCT/US2019/029966; dated Jul. 3, 2019; 10 pages.

(Continued)

*Primary Examiner* — Robert W Morgan
*Assistant Examiner* — Edward B Winston, III
(74) *Attorney, Agent, or Firm* — Maschoff Brennan

(57) ABSTRACT

Aligning image data of a patient with actual views of the patient using an optical code affixed to the patient. In some embodiments, a method may include affixing an optical code to a patient, affixing a pattern of markers to the patient, capturing image data of the patient, sensing the optical code affixed to the patient and a position of the optical code in a 3D space, accessing the image data, calculating the position of the pattern of markers in the 3D space, registering the position of the inner layer of the patient in the 3D space by aligning the calculated position of the pattern of markers in the 3D space with the position of the pattern of markers in the image data, and displaying in real-time, in an alternate reality (AR) headset, the inner layer of the patient from the image data projected onto actual views of the patient.

17 Claims, 9 Drawing Sheets

(56) References Cited

U.S. PATENT DOCUMENTS

2015/0187038 A1* 7/2015 Johnson ......... G06Q 10/063118
      705/3
2016/0324580 A1* 11/2016 Esterberg ............... A61B 5/055
2018/0092698 A1* 4/2018 Chopra ................... G06F 1/163
2018/0125584 A1   5/2018 Lang

OTHER PUBLICATIONS

Dean-Ben et al.; "Advanced Optoacoustic Methods for Multiscale Imaging of in Vivo Dynamics"; Royal Society of Chemistry; Oct. 25, 2016; located at: https://pubs.rsc.org/en/content/atriclehtml/2017/sc/c6cs00765a; 42 pages.

* cited by examiner

ALIGNING IMAGE DATA OF A PATIENT WITH ACTUAL VIEWS OF THE PATIENT USING AN OPTICAL CODE AFFIXED TO THE PATIENT

BACKGROUND

Augmented reality (AR) systems generally take a user's live view of a real-world environment and augment that view with computer-generated virtual elements such as video, sound, images, or graphics. As a result, AR systems function to enhance a user's current perception of reality.

One common problem faced by AR systems is accurately aligning the position of a virtual element with a live view of a real-world environment. Another common problem faced by AR systems is consistently retrieving the correct virtual element that corresponds to the live view of the real-world environment. These retrieval and alignment processes are often done manually which can be time consuming, cumbersome, and inaccurate.

The subject matter claimed herein is not limited to embodiments that solve any disadvantages or that operate only in environments such as those described above. Rather, this background is only provided to illustrate one example technology area where some embodiments described herein may be practiced.

SUMMARY

In some embodiments, a method for aligning image data of a patient with actual views of the patient using an optical code affixed to the patient may include various acts. For example, the method may include affixing an optical code to a patient, with the optical code being perceptible to an optical sensor. The method may also include affixing a pattern of markers to the patient in a fixed position relative to a position of the optical code, with the pattern of markers being perceptible to a non-optical imaging modality. The method may further include capturing image data of the patient using the non-optical imaging modality, with the image data including an inner layer of the patient and with the image data further including the pattern of markers in a fixed position relative to a position of the inner layer of the patient. The method may also include sensing, with an optical sensor of an augmented reality (AR) headset, the optical code affixed to the patient and a position of the optical code in a 3D space. The method may further include accessing, based on the optical code, the image data. The method may also include calculating, based on the sensed position of the optical code in the 3D space and the fixed position of the pattern of markers relative to the position of the optical code, the position of the pattern of markers in the 3D space. The method may further include registering, based on the calculated position of the pattern of markers in the 3D space and the fixed position in the image data of the pattern of markers relative to the position of the inner layer of the patient, the position of the inner layer of the patient in the 3D space by aligning the calculated position of the pattern of markers in the 3D space with the position of the pattern of markers in the image data. The method may also include displaying in real-time, in the AR headset and based on the registering, the inner layer of the patient from the image data projected onto actual views of the patient.

In some embodiments, the affixing of the optical code to the patient may include affixing a bandage with the optical code printed thereon to an outside layer of the patient. In these embodiments, the affixing of the pattern of markers to the patient in the fixed position relative to the position of the optical code may include the pattern of markers being affixed to the bandage in the fixed position relative to the position of the optical code. Also, in these embodiments, the pattern of markers may be embedded within the bandage, such as where the pattern of markers is embedded within an ink with which the optical code is printed on the bandage and the ink includes a material that is perceptible to the non-optical imaging modality. In these embodiments, the material that is perceptible to the non-optical imaging modality may be a radio-opaque material that is not transparent to X-rays, a magnetically visible material, or a radioactive material.

In some embodiments, the non-optical imaging modality may include a Magnetic Resonance Imaging (MRI) modality, a Computerized Tomography (CT) scan modality, an X-ray modality, a Positron Emission Tomography (PET) modality, an ultrasound modality, a fluorescence modality, an Infrared Thermography (IRT) modality, or a Single-Photon Emission Computed Tomography (SPECT) scan modality.

In some embodiments, the image data may include two-dimensional (2D) image data, three-dimensional (3D) image data, four-dimensional (4D) image data, or some combination thereof.

In some embodiments, the optical code may be a linear barcode, a matrix two-dimensional (2D) barcode, a Quick Response (QR) code, or some combination thereof.

In some embodiments, the optical code may be linked to medical data of the patient such that the medical data of the patient can be accessed with the optical code. In these embodiments, the optical code may be a security credential linked to medical data of the patient such that the medical data of the patient can be accessed with the optical code without additional security credentials.

In some embodiments, the affixing of the optical code to the patient may include printing the optical code on skin of the patient.

In some embodiments, the affixing of the optical code to the patient may include placing an article of clothing on the patient with the optical code printed thereon.

In some embodiments, an apparatus for aligning image data of a patient with actual views of the patient using an optical code affixed to the patient may include a bandage, an optical code printed on the bandage, and a pattern of markers affixed to the bandage. The optical code may be perceptible to an optical sensor. The pattern of markers may have a fixed position in the bandage relative to a position of the optical code on the bandage. The pattern of markers may be perceptible to a non-optical imaging modality such that when image data of the patient is captured using non-optical imaging modality, the image data includes an inner layer of the patient and the image data further includes the pattern of markers in a fixed position relative to the position of the inner layer of the patient.

In some embodiments, the pattern of markers may be embedded within an ink with which the optical code is printed on the bandage. In these embodiments, the ink may include a material that is perceptible to the non-optical imaging modality. In these embodiments, the material that is perceptible to the non-optical imaging modality may be a radio-opaque material that is not transparent to X-rays, a magnetically visible material, or a radioactive material.

In some embodiments, the bandage may be formed from a material that is sterilizable.

It is to be understood that both the foregoing summary and the following detailed description are explanatory and are not restrictive of the invention as claimed.

BRIEF DESCRIPTION OF THE DRAWINGS

Embodiments will be described and explained with additional specificity and detail through the use of the accompanying drawings in which.

DETAILED DESCRIPTION

Figure 1:
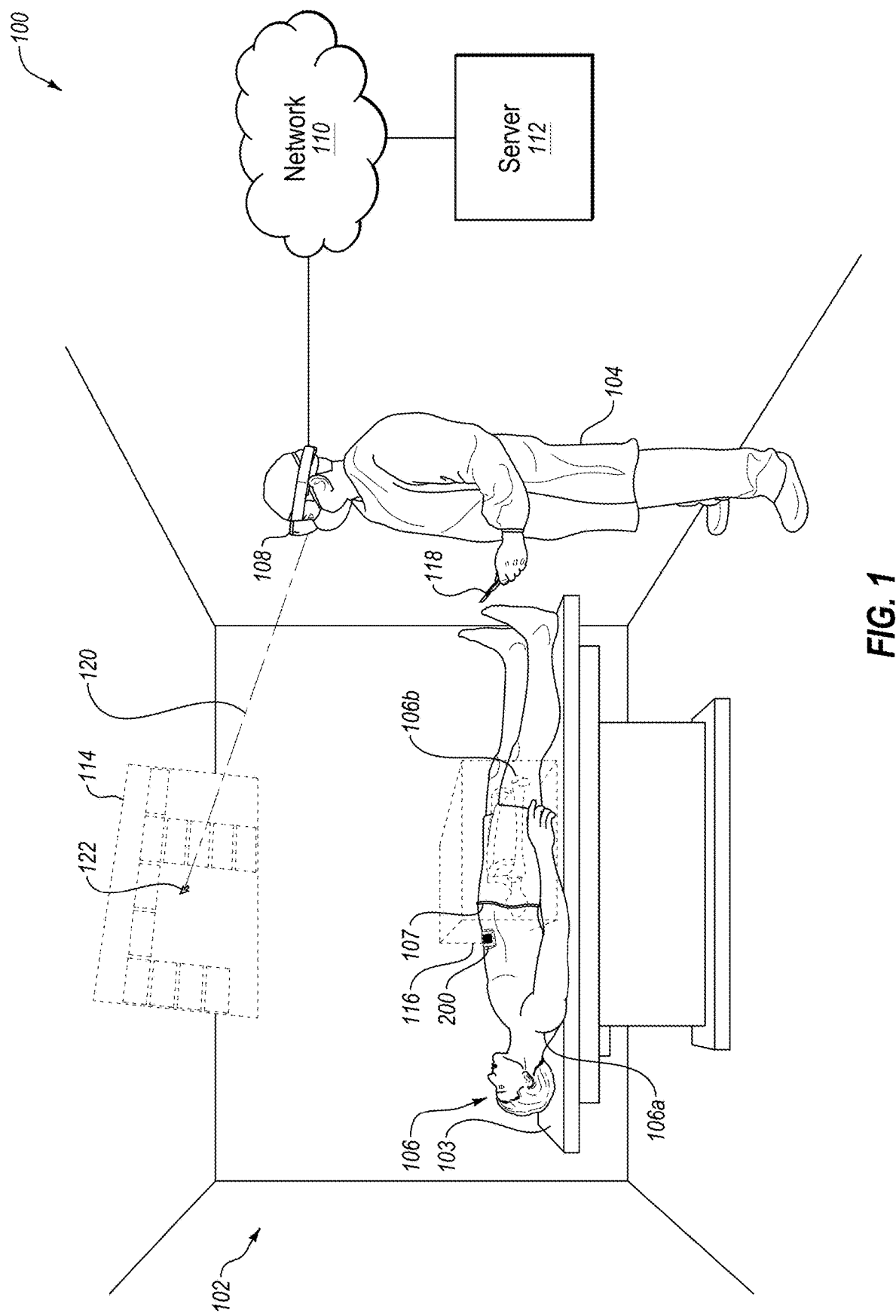
FIG. 1 illustrates an example augmented reality (AR) environment in which image data of a patient may be aligned with actual views of the patient using an optical code affixed to the patient.

Medical imaging may be employed to create visual representations of the interior of a patient. More particularly, medical imaging may be employed to reveal internal structures hidden by an outer layer of a patient, such as the skin or clothing of the patient, for various purposes such as training, research, diagnosis, and treatment.

Conventional medical imaging systems may create image data for a patient and then display that image data on a computer display. While viewing images of a patient on a computer display, detached from the actual patient, may be useful in training, research, diagnosis, and treatment, viewing, such detached viewing may also result in some problems.

For example, where a surgeon needs to remove a tumor from a patient's brain, the surgeon may view an image of the patient's brain on a computer display. After viewing the location of the tumor on the computer display, the surgeon may then shift his view from the computer display to the actual patient on an operating table and attempt to identify the approximate location on the actual patient of the tumor inside the patient's brain. This method of identifying the approximate location of the tumor can be difficult and error-prone. For example, the surgeon may accidentally identify the left side of the brain in the image as having the tumor when in reality the tumor is in the right side of the brain. This error may lead to the surgeon erroneously making an unnecessary incision on the left side of the patient's skull at the beginning of the brain surgery, or may lead to the surgeon erroneously guiding an instrument away from the tumor during the brain surgery.

In another example, where a doctor needs to perform knee surgery on a patient, the doctor may view an image of the patient's knee on a computer display. After viewing the problematic area of the knee on the computer display, the doctor may then shift his view from the computer display to the actual patient on an operating table and attempt to identify the problematic area of the knee on the actual patient for the surgery. This method of identifying the problematic area of the knee can be difficult and error-prone. For example, the doctor may accidentally pull up images of the wrong patient on the computer display, without realizing that the patient on the operating table does not match the images on the computer display. This error may lead to the surgeon erroneously making an incision in the wrong location due to natural variation of problematic areas of the knee from one patient to the next at the beginning of the knee surgery, or may lead to the surgeon erroneously guiding an instrument into the wrong internal area of the knee during the knee surgery.

To avoid the problems raised in the brain surgery and knee surgery examples discussed above, a medical professional may employ an augmented reality (AR) headset in order to augment actual views of a patient (e.g., real-time views of the patient that can be viewed with the naked eye of the user or with the eye of the user through a lens of an AR headset) with image data of the patient (e.g., one or more images previously captured and then projected onto a display such as onto a lens of an AR headset). In particular, image data of a patient may be aligned, or registered, with actual views of the patient and then images derived from the image data may be projected onto the actual views of the patient in an AR headset. Unfortunately, however, accurate alignment, or registration, of image data of a patient with the actual views of the patient can be difficult to accomplish because this alignment process is often done manually which can be time consuming, cumbersome, and inaccurate, and there exists the possibility that the wrong image data will be retrieved for a given patient.

One solution to the problem of manual alignment discussed above is the automatic alignment disclosed in U.S. Pat. No. 9,892,564, which is incorporated herein by reference in its entirety. However, this automatic alignment may be limited, in some applications, by the resolution of mapping sensors in an AR headset and/or where only a relatively small area of the skin or other outer layer of the patient is exposed.

The embodiments disclosed herein may provide various benefits over a conventional AR system. In particular, the embodiments disclosed herein may, for example, align image data of a patient with actual views of the patient using an optical code affixed to the patient. For example, a medical professional may affix an optical code, such as a QR code, as well as a pattern of markers, to a patient. Then, the medical professional may employ a non-optical imaging modality to capture image data of the patient. The image data may include one or more inner layers of the patient as well as the pattern of markers in a fixed position relative to a position of the one or more inner layers of the patient. Then, the medical professional may employ an AR headset to sense the optical code affixed to the patient and a position of the optical code in a 3D space. The AR headset may then automatically access the image data based on the optical code and may automatically calculate the position of the pattern of markers in the 3D space based on the sensed position of the optical code in the 3D space and the fixed position of the pattern of markers relative to the position of the optical code. The AR headset may then automatically register the position of the inner layer of the patient in the 3D space by aligning the calculated position of the pattern of markers in the 3D space with the position of the pattern of markers in the image data based on the calculated position of the pattern of markers in the 3D space and the fixed position in the image data of the pattern of markers relative to the position of the inner layer of the patient. Finally, the AR headset may display in real-time the one or more inner layers of the patient from the image data projected onto actual views of the patient.

Thus, the embodiments disclosed herein may enable a medical professional to view a virtual interior of the patient while looking at the actual patient through an AR headset without any time consuming, cumbersome, and inaccurate manual alignment of image data with actual views of the patient. Further, employing the same optical code as was used during the capturing of the image data to automatically retrieve the image data, such as retrieval during surgery, may ensure that the image data retrieved by the AR headset matches the actual patient being viewed through the AR headset without any time consuming, cumbersome, and inaccurate manual retrieval of image data. When used in training, research, diagnosis, or treatment, these embodiments may enable a medical professional to more easily and more accurately locate a target location within a patient. Further, the embodiments disclosed herein may enable automatic alignment with a relatively small area of the skin or other outer layer of the patient exposed, such as the relatively small area of the skin of the patient 106 that is exposed in FIG. 2.

For example, when employed in the brain surgery example discussed above, the embodiments disclosed herein may accurately align image data of a patient with actual views of the patient and then avoid the surgeon getting confused on the location of the tumor between the right and left sides of the brain, and may thereby avoid the surgeon making an unnecessary incision on the wrong side of the skull at the beginning of the brain surgery. Further, the embodiments disclosed herein may enable the surgeon to accurately internally guide an instrument toward the tumor during the surgery to remove the tumor. Similarly, when employed in the knee surgery example discussed above, the embodiments disclosed herein may avoid the doctor using image data for the wrong patient because the optical code that remains affixed to the patient may be employed by the AR headset to automatically retrieve the image data that was previously captured of the patient with the same optical code affixed to the patient at the beginning of the knee surgery. Further, the embodiments disclosed herein may enable the surgeon to accurately guide an instrument toward a desired internal area of the knee during the knee surgery.

Turning to the figures, FIG. 1 illustrates an example augmented reality (AR) environment 100 in which image data of a patient 106 may be aligned with actual views of the patient 106 using an optical code 200 affixed to the patient 106. In some embodiments, the environment 100 may include a 3D space 102, a user 104, the patient 106, an AR headset 108 which may be in communication with a server 112 over a network 110, and an optical code 200. In some embodiments, the environment 100 may also include a virtual user interface 114, a virtual box 116, an object 118, and a virtual cursor 122, all shown in dashed lines to indicate that these virtual elements are generated by the AR headset 108 and only viewable by the user 104 through the AR headset 108.

In some embodiments, the 3D space 102 may be any 3D space including, but not limited to, a room of a building such as an operating room with an operating table 103 (as illustrated in FIG. 1), an office, a classroom, or a laboratory.

In some embodiments, the 3D space 102 may be a space where the user 104 may view the patient 106 while wearing the AR headset 108.

In some embodiments, the user 104 may be any user of the AR headset 108 including, but not limited to, a medical professional (as illustrated in FIG. 1), an instructor, a researcher, a patient, or a caregiver of a patient. For example, a medical professional may use the AR headset 108 in order to perform a medical procedure on the patient 106, such as surgery on the patient 106. Similarly, a researcher or an instructor may use the AR headset 108 while performing medical research or instructing medical students. Further, a caregiver of the patient 106, or the patient 106 himself, may use the AR headset 108 when a medical professional is attempting to explain a suggested medical procedure for the patient 106.

In some embodiments, the patient 106 may be any animal, either conscious or unconscious, either living or dead, either whole or missing one or more body parts. For example, the patient 106 may be a living human adult (as illustrated in FIG. 1) who has been rendered unconscious in order to undergo a medical procedure by the user 104. In another example, the patient 106 may be a cadaver of a human adult that will undergo a dissection for research or training purposes. In another example, the patient 106 may be a conscious animal that is being evaluated by a veterinarian in order to diagnose a medical condition. In another example, the patient 106 may be a single limb or organ of a deceased human.

In some embodiments, the AR headset 108 may be any computer system in the form of an AR headset that is capable of augmenting actual views of the patient 106 with image data. For example, the AR headset 108 may be employed by the user 104 in order to augment actual views of the patient 106 with one or more inner layers of the patient 106 including, but not limited to, bones 106b (as illustrated in FIG. 1), muscles, organs, or fluids. In some embodiments, the AR headset 108 may perform this augmenting of actual views of the patient 106 regardless of the current position of the user 104 in the 3D space 102. For example, the user 104 may walk around the operating table 103 and view the patient 106 from any angle within the 3D space 102, and all the while the AR headset 108 may continually augment actual views of the patient 106 with one or more inner layers of the patient 106, so that both the patient 106 and the image data of the patient 106 may be viewed by the user 104 from any angle within the 3D space 102. The AR headset 108 may perform this augmenting of actual views of the patient 106 with image data according to the method 400 disclosed herein in connection with FIG. 4. In some embodiments, the AR headset 108 may be a modified version of the Microsoft HoloLens.

In some embodiments, the network 110 may be configured to communicatively couple the AR headset 108 and the server 112 or other computer system(s). In some embodiments, the network 110 may be any wired or wireless network, or combination of multiple networks, configured to send and receive communications between systems and devices. In some embodiments, the network 110 may include a Personal Area Network (PAN) such as a Bluetooth network, a Local Area Network (LAN) such as a WiFi network, a Metropolitan Area Network (MAN), a Wide Area Network (WAN), or a Storage Area Network (SAN). In some embodiments, the network 110 may also be coupled to, or may include, portions of a telecommunications network for sending data in a variety of different communication protocols, such as a cellular network.

In some embodiments, the server 112 may be any computer system capable of functioning in connection with the AR headset 108. In some embodiments, the server 112 may be configured to communicate in real-time with the AR headset 108 in order to convey image data to, or receive data from, the AR headset 108. In addition, the server 112 may be employed to offload some or all of the data storage or processing desired by the AR headset 108.

In some embodiments, the virtual user interface 114 may be any virtual user interface generated by the AR headset 108 that includes options for altering the display of the projected inner layer(s) of the patient 106 from the image data of the patient 106. The virtual user interface 114 may further include other information that may be useful to the user 104. For example, the virtual user interface 114 may include real-time vital signs for the patient 106 such as heart-rate, blood-pressure, and respiration-rate. In another example, the virtual user interface 114 may include a stopwatch showing the amount of time the patient 106 has been unconscious. In another example, the virtual user interface 114 may include medical charts or other medical data of the patient 106.

In some embodiments, the virtual box 116 may be generated by the AR headset 108 to confine within a volume of the virtual box 116 the projected inner layer of the patient 106 from the image data. For example, the projected bones 106*b* of the patient 106 may be confined within the virtual box 116 in FIG. 1. In some embodiments, the virtual box 116 may also assist the user when navigating the projected image data by providing a frame of reference for the user 104. For example, this frame of reference may assist the user when moving axial slices, coronal slices, sagittal slices, or oblique slices of the image data within the virtual box 116. Slices may be two-dimensional (2D) slices and/or 3D slices. 3D slices may include curved slices, such as curved slices that follow the natural curve of an anatomical feature, or slices that have a depth as well as a height and width. The user 104 may move these slices using hand gestures that require the user 104 to generally move his hand in the directions of the lines of the virtual box 116, so the display of the virtual box 116 may make these hand movements easier for the user 104.

In some embodiments, the object 118 may be anything that the user 104 wishes to insert into the patient 106 though an outer layer of the patient 106. For example, the object 118 may include, but is not limited to, a scalpel (as illustrated in FIG. 1), a scope, a drill, a probe, another medical instrument, or even the hand of the user 104. Similar to the registration of the real-time position of the outer layer of the patient 106, the position of the outer layer of the object 118 may also be registered. However, unlike the patient 106, which may remain relatively still in the environment 100, the object 118 may be frequently moved in the environment 100, such that the real-time position of the object 118 may be automatically tracked in the 3D space 102 with respect to the registered positions of the outer layer of the patient 106. Then, in the event that the user 104 inserts some portion of the object 118 into the outer layer of the patient 106, the AR headset 108 may display a virtual inserted portion of the object 118 projected into the projected inner layer of the patient 106 from the image data. In this manner, the virtual inserted portion of the object 118 may be projected onto actual views of the user 104 even when the actual inserted portion of the object 118 is hidden from the actual views of the user 104. The registration of the object 118 may be performed in a manner similar to the registration of the image data disclosed herein, in which an optical code is affixed to the object 118, and then the optical code is sensed by the AR headset 108 to establish a continually updating position of the object 118 with respect to the 3D space 102.

In some embodiments, the virtual cursor 122 may be a virtual cursor generated by the AR headset 108 on the virtual user interface 114, on another virtual control, or at any other position in the 3D space 102. In some embodiments, the position of the virtual cursor 122 may correspond to a focal orientation 120 of the AR headset 108, which may correspond to the orientation of the head of the user 104. The virtual cursor 122 may be employed by the user 104 to select one or more options of the virtual user interface 114, sometimes in connection with one or more other actions by the user 104, such as a blink of the user's eyes, or one or more hand gestures of the user 104, such as the tapping together of two fingers in the field of view of the AR headset 108.

In some embodiments, the optical code 200 may be affixed to the patient 106 prior to the generation of image data of the patient 106, and then remain affixed to the patient 106 while the patient 106 is being viewed by user 104 through the AR headset 108. In other embodiments, the optical code 200 may be affixed to the patient 106 after the generation of image data of the patient 106, and then remain affixed to the patient 106 while the patient 106 is being viewed by user 104 through the AR headset 108. In either case, the optical code 200 may then be employed by the AR headset 108 to automatically align the image data of the patient 106 with actual views of the patient 106. Further, when employing the same optical code 200 as was used during the capturing of the image data to automatically retrieve the image data, doing so may ensure that the image data retrieved by the AR headset 108 matches the actual patient 106 being viewed through the AR headset 108. Additional aspects of the optical code 200 will be discussed below in connection with FIG. 2.

Modifications, additions, or omissions may be made to the environment 100 without departing from the scope of the present disclosure. For example, in some embodiments, multiple users each wearing an AR headset 108 may be simultaneously present in the 3D space 102 in order to simultaneously view the patient 106 augmented with image data of the patient 106. In another example, multiple patients may be simultaneously present in the 3D space 102 in order to allow the user 104 wearing the AR headset 108 to simultaneously view the multiple patients augmented with image data of the patients. In another example, multiple users each wearing an AR headset 108 and multiple patients may simultaneously be present in the 3D space. In another example, video of the view from the AR headset 108 may be captured by the AR headset 108 and then sent to a remote location, such as to the server 112 over the network 110 or to a remote AR headset or Virtual Reality (VR) headset for viewing by another user. This example may enable the remote user to guide the local user 104 through a medical procedure on the patient 106. Further, although the environment 100 is generally disclosed to be in the context of a user 104 viewing a patient 106, it is understood that the environment 100 may be more broadly defined as any environment where a user wishes to view one or more inner layers of any object, such as a tree, a rock, an oilfield, or a planet.

Figure 2:
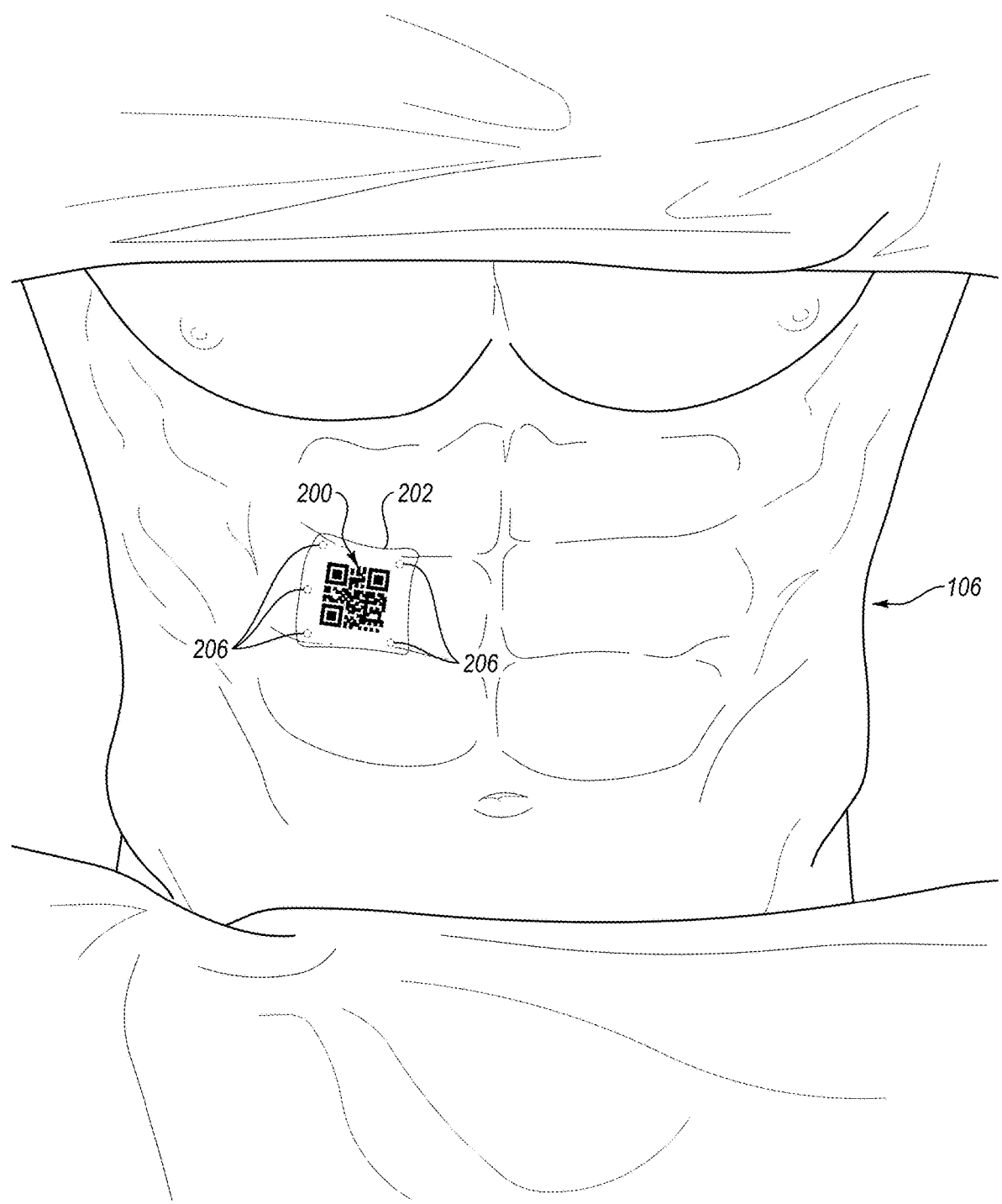
FIG. 2 illustrates the optical code of FIG. 1 affixed to a patient.

FIG. 2 illustrates the optical code 200 of FIG. 1 affixed to the patient 106 of FIG. 1. With reference to both FIG. 1 and FIG. 2, the optical code 200 may be perceptible to an optical sensor, such as an optical sensor built into the AR headset 108. In some embodiments, the optical code 200 may be a linear barcode, a matrix two-dimensional (2D) barcode, a Quick Response (QR) code, or some combination thereof. In some embodiments, the optical code 200 may be linked to medical data of the patient 106 such that the medical data of the patient 106 can be accessed with the optical code 200. In these embodiments, the optical code may be a security credential linked to medical data of the patient 106 such that the medical data of the patient 106 can be accessed with the optical code 200 without additional security credentials. In these embodiments, using the optical code 200 itself as a security credential may allow the user of the AR headset 108 to access medical images and other sensitive medical data of the patient 106 in a medical environment (such as during a surgery on the patient 106) without requiring the user 104 to manually or otherwise enter other security credential(s) prior to accessing the medical data of the patient 106. In other words, the automatic sensing of the optical code 200 by the AR headset 108 may provide instant and automatic access to medical image data and other medical data of the patient 106 without any additional effort on the part of the user 104 of the AR headset 108, based on an assumption that any user with direct access to the optical code 200 is authorized to have direct access to the medical data of the patient 106 without any additional authentication.

The optical code 200 may further be associated with markers 206 that are perceptible to a non-optical imaging modality. Examples of a non-optical imaging modality may include, but are not limited to, a Magnetic Resonance Imaging (MRI) modality, a Computerized Tomography (CT) scan modality, an X-ray modality, a Positron Emission Tomography (PET) modality, an ultrasound modality, a fluorescence modality, an Infrared Thermography (IRT) modality, or a Single-Photon Emission Computed Tomography (SPECT) scan modality. Forming the markers 206 from a material that is perceptible to a non-optical imaging modality may enable the markers 206 to appear in any image data of the patient 106 that is captured using a non-optical imaging modality. Examples of markers 206 include, but are not limited to, metal spheres, liquid spheres, metal threads, and sections of metallic ink.

The markers 206 may be arranged in a pattern that has a fixed position relative to a position of the optical code 200. For example, in the embodiment disclosed in FIG. 2, the optical code 200 may be printed on a bandage 202 (such as an adhesive bandage) and the markers 206 may be affixed to the bandage 202 (such as by being embedded in the bandage 202 so as to not be visible on any surface of the bandage). In this embodiment, the markers 206 may be arranged in a pattern that has a fixed position relative to a position of the optical code 200 by being arranged in the fixed pattern in the bandage 202. Additionally or alternatively, the markers 206 may be embedded within the optical code 200 itself, such as where the markers 206 are embedded within an ink with which at least some portion of the optical code 200 is printed on the bandage 202 and the ink includes a material that is perceptible to the non-optical imaging modality, such as an ink that is radio-opaque and thus not transparent to X-rays, an ink that is magnetically visible to thus be visible on an MRI image, or an ink that is radioactive to thus be visible on a PET image. In these embodiments, the optical code 200 itself may serve both as an optical code and as the pattern of markers. Additionally or alternatively, the markers 206 may be arranged in a manner that does not involved affixing the markers 206 to a bandage upon which the optical code 200 is printed, such as by printing the optical code 200 onto an article of clothing (such as clothing 107) and affixing the markers 206 to the article of clothing, or by printing (at least temporarily) the optical code 200 directly on the skin 106a of the patient 106 and affixing (at least temporarily) the markers 206 directly to, or underneath, the skin 106a of the patient 106. In any of these embodiments, by arranging the markers 206 in a pattern that has a fixed position relative to a position of the optical code 200, this fixed position may later be employed to calculate the location of the pattern of the markers 206 with respect to a visible location of the optical code 200, even where the markers 206 are not themselves visible or otherwise perceptible to other sensors of the AR headset 108.

Further, in some embodiments, one or more additional internal markers may be inserted within the patient 106. For example, one or more additional internal markers may be inserted into a breast of the patient 106 at the site of a biopsied mass in order to enable tracking of the internal biopsy site. These one or more additional internal markers may then be located and triangulated with the pattern of markers 206 to help locate the internal biopsy site. This may be particularly useful in situations where an internal site to be tracked is in a part of the body of the patient 106 that is less fixed with respect to the rest of the body of the patient, such as a breast (which tends to shift around depending on the position of the patient 106).

Once the optical code 200 and the markers 206 are affixed to the patient 106 in a fixed pattern, a medical professional or automated system may employ the non-optical imaging modality (to which the markers 206 are perceptible) to capture image data of the patient 106 and of the markers 206. In particular, the image data may include one or more inner layers (such as bones 106b, muscles, organs, or fluids) of the patient 106, as well as including the pattern of markers 206 in a fixed position relative to the positions of the one or more inner layers of the patient 106. In other words, not only will the one or more inner layers of the patient 106 appear in the image data of the patient 106, but the markers 206 will also appear in the image data of the patient 106 in a fixed pattern, and the position of this fixed pattern of the markers 206 will appear in the image data in a fixed position relative to the positions of the one or more inner layers of the patient 106. In one example, where the non-optical imaging modality is a CT scan modality, the CT scan images may display the bones 106b, organs, and soft tissues of the patient 106, as well as the markers 206 arranged in a fixed position with respect to the positions of the bones 106b, organs, and soft tissues of the patient 106.

Once the image data of the patient 106 is captured, a period of time may pass with the optical code remaining affixed to the patient. During the period of time, the patient 106 may be moved, for example, from a medical imaging room in a hospital to an operating room in the hospital. In some embodiments, the bandage 202 may be formed from a material that is sterilizable in order to facilitate leaving the bandage 202 affixed to the patient 106 first in a non-sterile environment (such as an x-ray room) as well as later in a sterile environment (such as an operating room) where the bandage 202 must be sterilized while already affixed to the patient 106. After this period of time passes, a user 104 (such as a medical professional) may employ the AR headset 108 to determine a location of the optical code 200 in the 3D space 102. For example, the AR headset 108 may include an optical sensor, such as a camera, which the AR headset 108 may employ to sense the optical code 200 affixed to the patient 106, as well as sensing the position of the optical code 200 in the 3D space 102. Next, the AR headset 108 may access the image data of the patient 106 based on the optical code. For example, as discussed above, as soon as the AR headset 108 senses the presence of the optical code 200 in the 3D space 102, the AR headset 108 may automatically retrieve the image data of the patient 106 without requiring any additional credential from the user 104 of the AR headset 108.

After sensing the presence of the optical code 200 in the 3D space 102, the AR headset 108 may automatically calculate the position of the pattern of the markers 206 in the 3D space 102. This automatic calculation may be based on the sensed position of the optical code 200 in the 3D space 102 and may also be based on the known fixed position of the pattern of the markers 206 relative to the position of the optical code 200. In other words, even where the markers 206 are not perceptible to the AR headset 108 (for example, due to the markers 206 being embedded within the bandage 202), the AR headset 108 can automatically calculate the location of the pattern of the markers 206 based on the position of the optical code 200 that is sensed by the AR headset 108 and based on the fixed position of the pattern of the markers 206 relative to the position of the optical code 200 that is known to the AR headset 108. In this example, as long as the optical code 200 remains affixed to the patient 106 in the same location between the capturing of the image data and the sensing of the optical code 200 by the AR headset 108, and as long as the position of the pattern of the markers 206 remains fixed with respect to the position of the optical code 200, these fixed positions may enable the AR headset 108 to automatically calculate the position of the pattern of the markers 206 in the 3D space 102 even where the AR headset 108 is not capable of directly sensing the positions of the markers 206 in the 3D space 102.

After calculating the location of the pattern of the markers 206 in the 3D space 102, the AR headset 108 may then register, based on the calculated position of the pattern of the markers 206 in the 3D space 102 and the fixed position in the image data of the pattern of the markers 206 relative to the positions of the one or more inner layers of the patient 106, the position of the one or more inner layers of the patient 106 in the 3D space 102 by aligning the calculated position of the pattern of the markers 206 in the 3D space 102 with the position of the pattern of the markers 206 in the image data. This alignment and registration may then enable the AR headset 108 to display in real-time the one or more inner layers of the patient 106 from the image data projected onto actual views of the patient 106.

Thus, the optical code 200, and the associated pattern of the markers 206, may be employed by the AR headset 108 to automatically align the image data of the patient 106 with actual views of the patient 106. Further, employing the same optical code 200 to automatically retrieve the image data as was used during the capturing of the image data may ensure that the image data retrieved by the AR headset 108 matches the actual patient 106 being viewed through the AR headset 108.

Modifications, additions, or omissions may be made to the optical code 200 as affixed to the patient 106 without departing from the scope of the present disclosure. For example, in some embodiments, multiple optical codes 200 may be simultaneously affixed to the patient 106 in order to further ensure accurate alignment of image data of the patient 106 with actual views of the patient 106 in the 3D space 102. In these embodiments, three or more optical codes 200 may enable triangulation based on the multiple optical codes 200. In these embodiments, spacing the multiple optical codes 200 apart, by several inches for example, may increase the accuracy of the triangulation. Also, in some embodiments, the pattern of five markers 206 disclosed in FIG. 2 may be replaced with another pattern, such as a pattern of three markers or a pattern of seven markers. Further, in some embodiments, since the markers 206 are affixed to an outside layer of the patient 106, and since the outside layer of the patient 106 may not be planar, the markers 206 may not all lie in a single plane, but instead may curve around any curvatures of the outside layer of the patient 106. In these embodiments, the fixed position of the pattern of the markers 206 relative to a position of the optical code 200 may be established after affixing the optical code 200 and the markers 206 to the patient 106 since this fixed position may be altered depending on any curvatures on the outside layer of the patient 106 to which the optical code 200 and the markers 206 are affixed.

Figure 5A:
FIGS. 5A-5B are photographs of an optical code and a pattern of markers affixed to a patient.
Figure 5B:
Figure 5C:
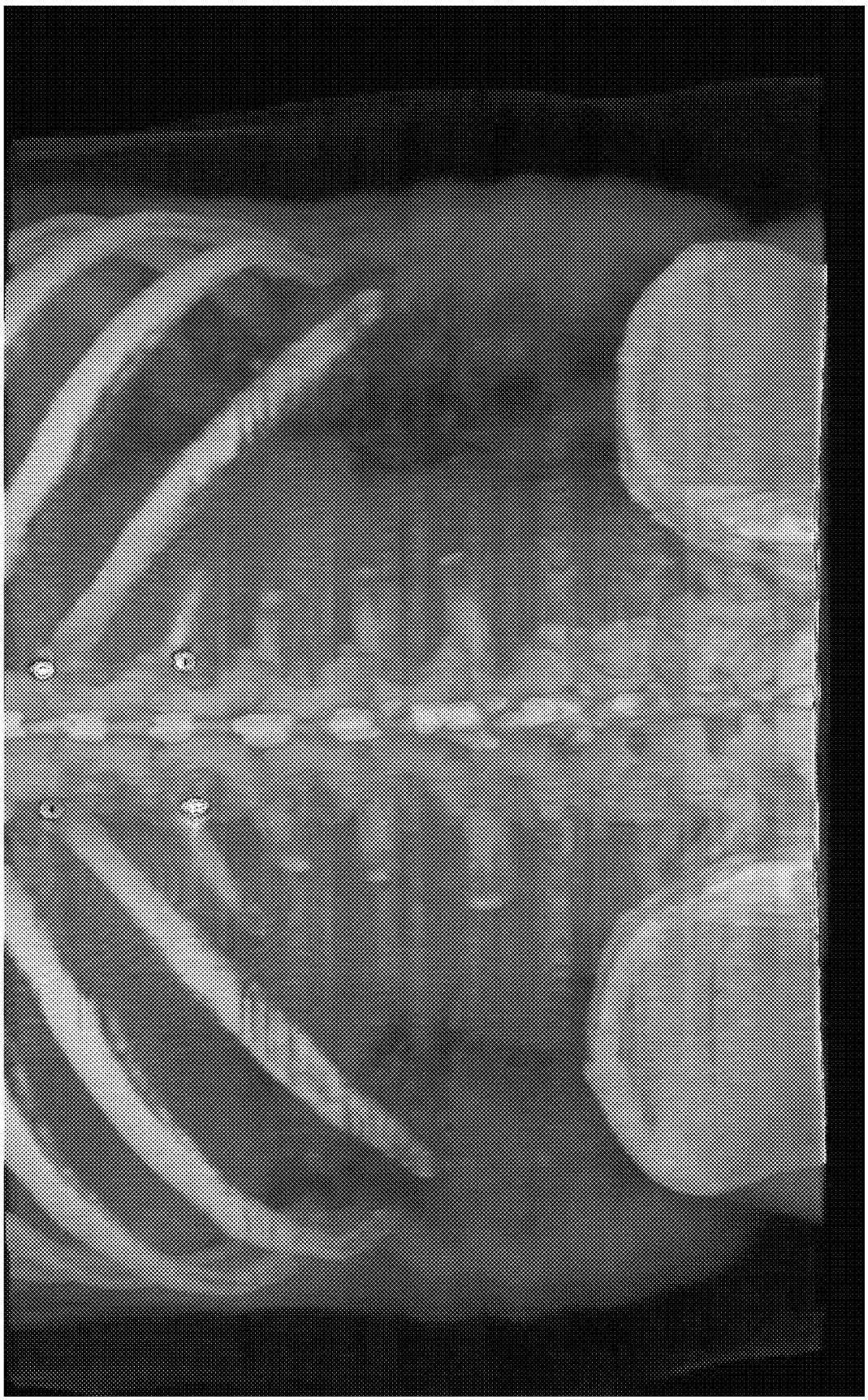
FIGS. 5C-5D are photographs of image data of the patient with the pattern of markers from FIGS. 5A-5B visible in the image data.
Figure 5D:
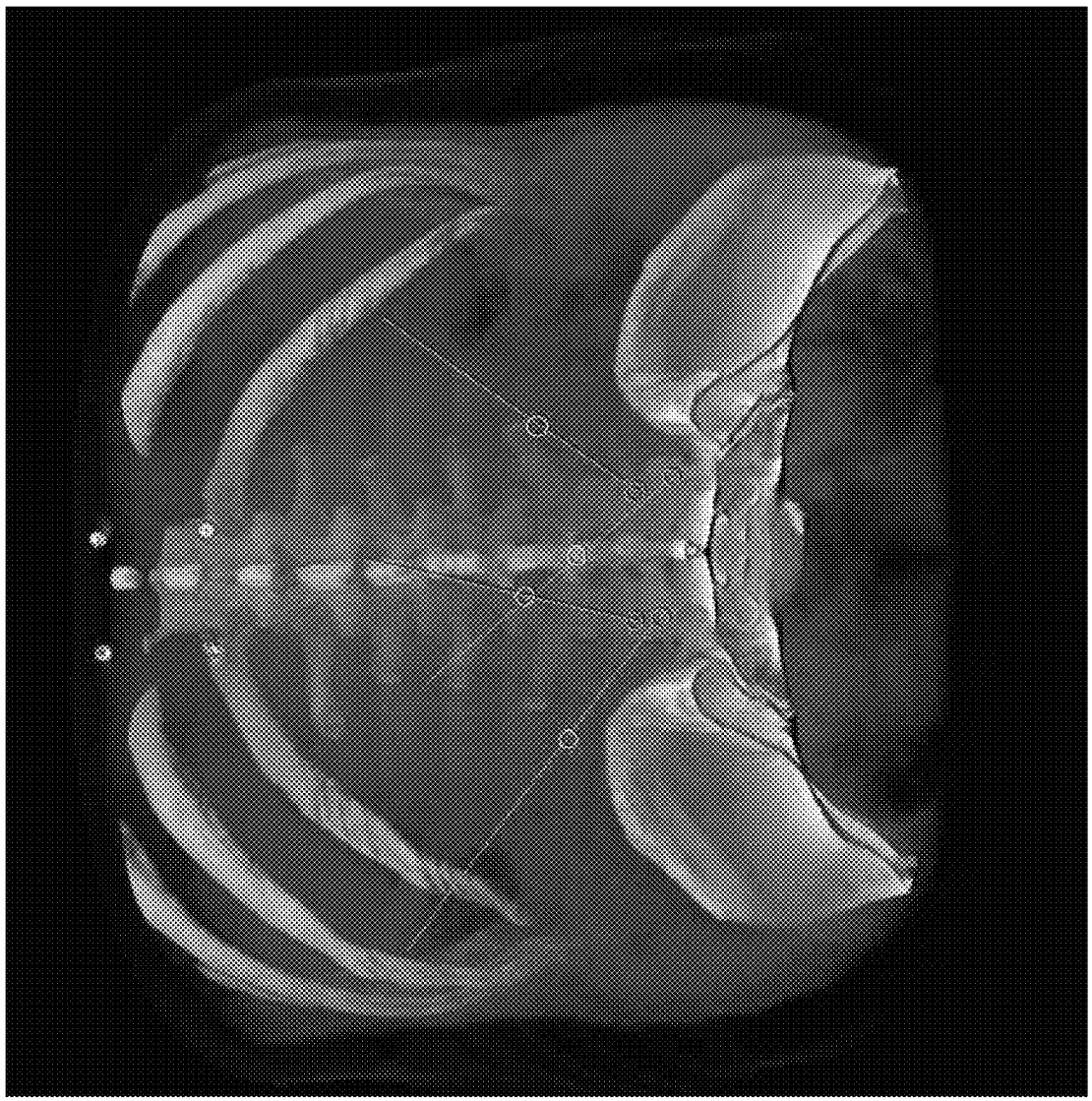
Figure 5E:
FIG. 5E is a photograph of a view through an augmented reality (AR) headset of the image data of FIGS. 5C-5D projected in real-time onto actual views of the patient of FIGS. 5A-5B.

FIGS. 5A-5B are photographs of an optical code and a pattern of markers affixed to a patient, FIGS. 5C-5D are photographs of image data of the patient with the pattern of markers from FIGS. 5A-5B visible in the image data, and FIG. 5E is a photograph of a view through an augmented reality (AR) headset of the image data of FIGS. 5C-5D projected in real-time onto actual views of the patient of FIGS. 5A-5B. As disclosed in FIGS. 5A-5B, a bandage may be affixed to a patient, with an optical code (e.g., a QR code) printed on the bandage, and a pattern of markers (e.g., four metal spheres) affixed to the bandage. The optical code may be perceptible to an optical sensor. The pattern of markers may have a fixed position in the bandage relative to a position of the optical code on the bandage. The pattern of markers may be perceptible to a non-optical imaging modality (e.g., a CT modality). Then, as disclosed in FIGS. 5C-5D, when image data (e.g., CT images) of the patient is captured using the non-optical imaging modality (e.g., the CT modality), the image data may include an inner layer of the patient (e.g., bones of the patient) and the image data may further includes the pattern of markers (e.g., the four metal spheres) in a fixed position relative to the position of the inner layer of the patient. Later, a user may wear an AR headset (e.g., a surgeon may wear the AR headset 108 of FIG. 1 during a surgery on the patient), and an optical sensor of the AR headset may sense the optical code affixed to the patient and a position of the optical code in a 3D space (e.g., an operating room). Then, the AR headset may access, based on the optical code, the image data of FIGS. 5C-5D. Next, the AR headset may calculate, based on the sensed position of the optical code in the 3D space and the fixed position of the pattern of markers (e.g., the four metal spheres) relative to the position of the optical code, the position of the pattern of markers in the 3D space. Then, the AR headset may register, based on the calculated position of the pattern of markers (e.g., the four metal spheres) in the 3D space and the fixed position in the image data (e.g., the CT images of FIGS. 5C-5D) of the pattern of markers relative to the position of the inner layer of the patient (e.g., the bones of the patient), the position of the inner layer of the patient in the 3D space by aligning the calculated position of the pattern of markers in the 3D space with the position of the pattern of markers in the image data. Next, as disclosed in FIG. 5E, the AR headset may display in real-time, in the AR headset and based on the registering, the view shown in the photograph of FIG. 5E, which is the inner layer of the patient (e.g., the bones of the patient) from the image data (e.g., the CT images of FIGS. 5C-5D) projected onto actual views of the patient.

Modifications, additions, or omissions may be made to the optical code and the pattern of markers disclosed in FIGS. 5A-5B, or to the image data disclosed in FIGS. 5C-5D, without departing from the scope of the present disclosure. For example, instead of a pattern of markers that includes four metal spheres, the pattern of markers in FIGS. 5A-5B may be replaced with another pattern of markers with a different number and/or a different type of markers, resulting in the other pattern of markers being included in the image data of FIGS. 5C-5D.

Figure 3:
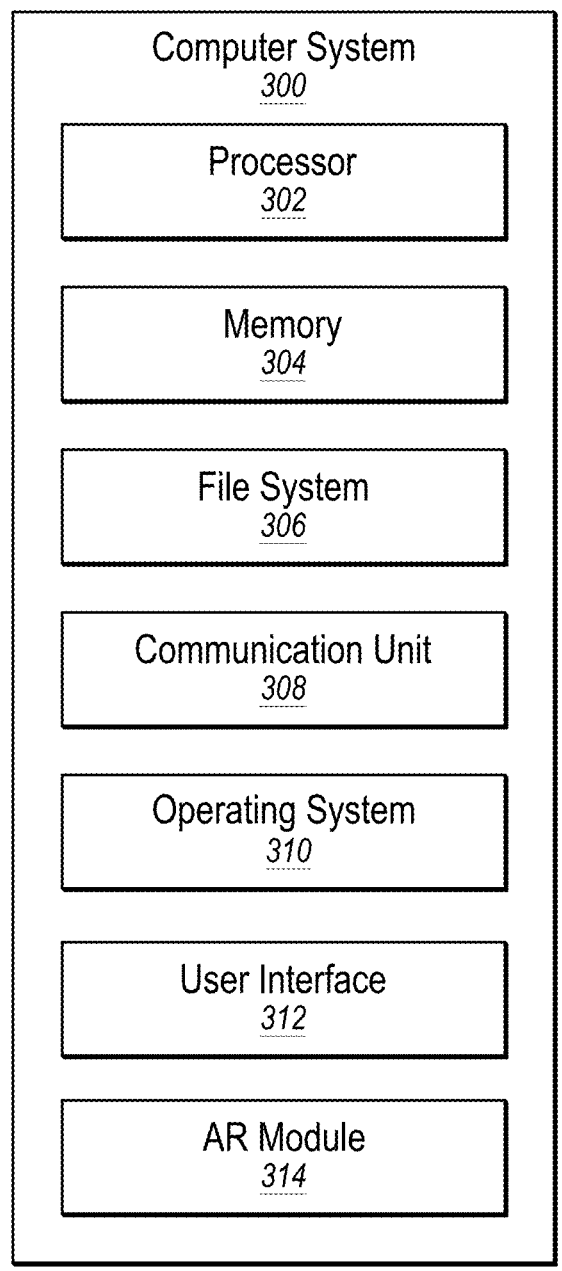
FIG. 3 illustrates an example computer system that may be employed in aligning image data of a patient with actual views of the patient using an optical code affixed to the patient.

FIG. 3 illustrates an example computer system 300 that may be employed in aligning image data of a patient with actual views of the patient using an optical code affixed to the patient. In some embodiments, the computer system 300 may be part of any of the systems or devices described in this disclosure. For example, the computer system 300 may be part of any of the AR headset 108 or the server 112 of FIG. 1.

The computer system 300 may include a processor 302, a memory 304, a file system 306, a communication unit 308, an operating system 310, a user interface 312, and an AR module 314, which all may be communicatively coupled. In some embodiments, the computer system 300 may be, for example, a desktop computer, a client computer, a server computer, a mobile phone, a laptop computer, a smartphone, a smartwatch, a tablet computer, a portable music player, an embedded computer, an AR headset, a VR headset, or any other computer system.

Generally, the processor 302 may include any suitable special-purpose or general-purpose computer, computing entity, or processing device including various computer hardware or software modules and may be configured to execute instructions stored on any applicable computer-readable storage media. For example, the processor 302 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data, or any combination thereof. In some embodiments, the processor 302 may interpret and/or execute program instructions and/or process data stored in the memory 304 and/or the file system 306. In some embodiments, the processor 302 may fetch program instructions from the file system 306 and load the program instructions into the memory 304. After the program instructions are loaded into the memory 304, the processor 302 may execute the program instructions. In some embodiments, the instructions may include the processor 302 performing one or more actions of the method 400 of FIG. 4.

The memory 304 and the file system 306 may include computer-readable storage media for carrying or having stored thereon computer-executable instructions or data structures. Such computer-readable storage media may be any available non-transitory media that may be accessed by a general-purpose or special-purpose computer, such as the processor 302. By way of example, and not limitation, such computer-readable storage media may include non-transitory computer-readable storage media including Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage media which may be used to carry or store desired program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause the processor 302 to perform a certain operation or group of operations, such as one or more actions of the method 400 of FIG. 4. These computer-executable instructions may be included, for example, in the operating system 310, in one or more applications, such as the AR module 314, or in some combination thereof.

The communication unit 308 may include any component, device, system, or combination thereof configured to transmit or receive information over a network, such as the network 110 of FIG. 1. In some embodiments, the communication unit 308 may communicate with other devices at other locations, the same location, or even other components within the same system. For example, the communication unit 308 may include a modem, a network card (wireless or wired), an infrared communication device, a wireless communication device (such as an antenna), and/or chipset (such as a Bluetooth device, an 802.6 device (e.g., Metropolitan Area Network (MAN)), a WiFi device, a WiMax device, a cellular communication device, etc.), and/or the like. The communication unit 308 may permit data to be exchanged with a network and/or any other devices or systems, such as those described in the present disclosure.

The operating system 310 may be configured to manage hardware and software resources of the computer system 300 and may be configured to provide common services for the computer system 300.

The user interface 312 may include any device configured to allow a user to interface with the computer system 300. For example, the user interface 312 may include a display, such as an LCD, LED, or other display, such as an AR lens, that is configured to present video, text, application user interfaces, and other data as directed by the processor 302. The user interface 312 may further include a mouse, a track pad, a keyboard, a touchscreen, volume controls, other buttons, a speaker, a microphone, a camera, any peripheral device, or other input or output device. The user interface 312 may receive input from a user and provide the input to the processor 302. Similarly, the user interface 312 may present output to a user.

Figure 4:
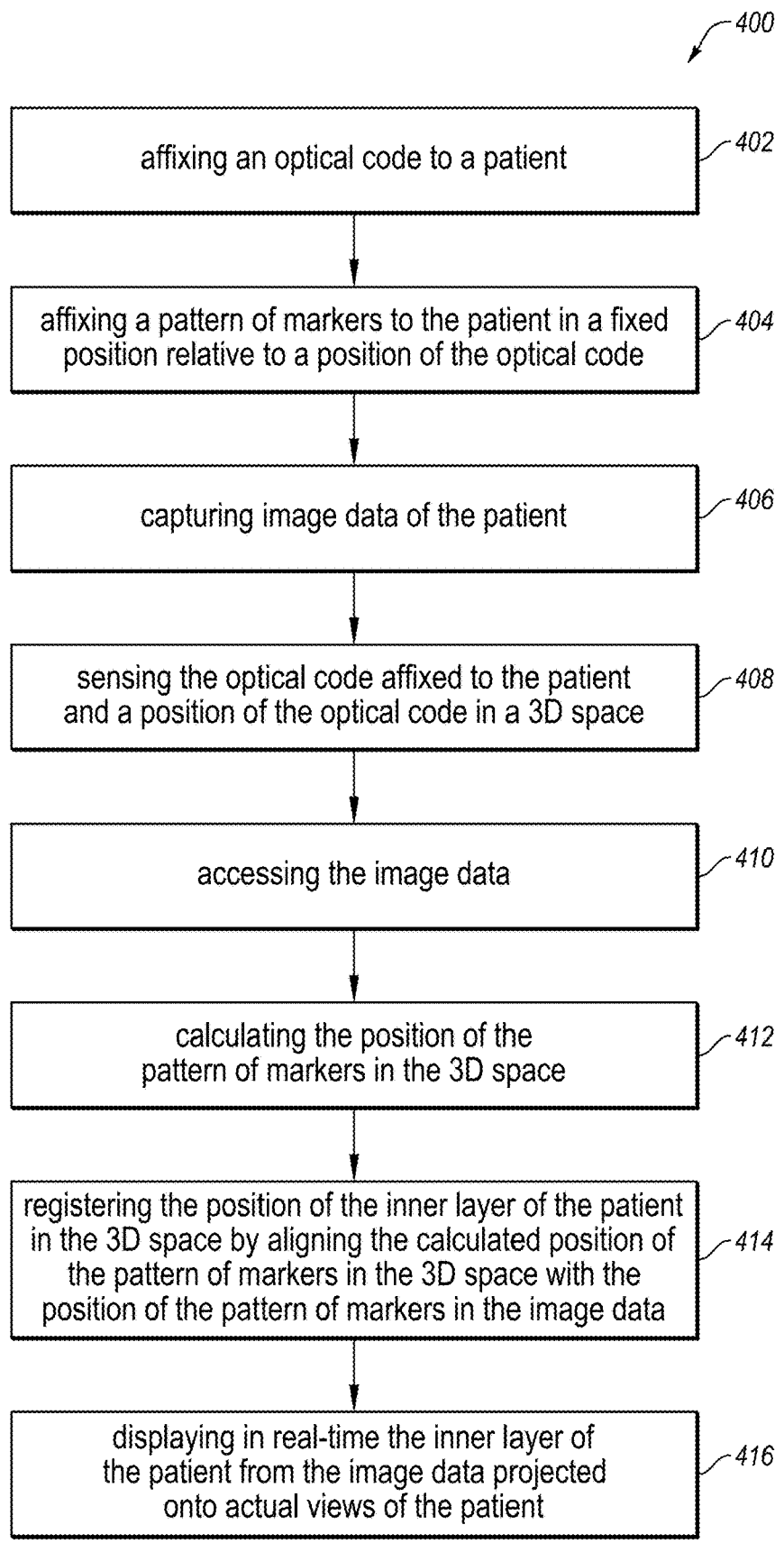
FIG. 4 is a flowchart of an example method of aligning image data of a patient with actual views of the patient using an optical code affixed to the patient.

The AR module 314 may be one or more computer-readable instructions stored on one or more non-transitory computer-readable media, such as the memory 304 or the file system 306, that, when executed by the processor 302, is configured to perform one or more methods, such as one or more of the actions of the method 400 of FIG. 4. In some embodiments, the AR module 314 may be part of the operating system 310 or may be part of an application of the computer system 300, or may be some combination thereof.

Modifications, additions, or omissions may be made to the computer system 300 without departing from the scope of the present disclosure. For example, although each is illustrated as a single component in FIG. 3, any of the components 302-314 of the computer system 300 may include multiple similar components that function collectively and are communicatively coupled. Further, although illustrated as a single computer system, it is understood that the computer system 300 may include multiple physical or virtual computer systems that are networked together, such as in a cloud computing environment, a multitenancy environment, or a virtualization environment.

FIG. 4 is a flowchart of an example method of aligning image data of a patient with actual views of the patient using an optical code affixed to the patient. The method 400 may be performed, in some embodiments, by a device or system, such as by the AR module 314 of FIG. 3 executing on the AR headset 108 and/or on the server 112 of FIG. 1. In these and other embodiments, the method 400 may be performed by one or more processors based on one or more computer-readable instructions stored on one or more non-transitory computer-readable media. The method 400 will now be described in connection with FIGS. 1, 2, 3, and 4. Although various actions of the method 400 are described below as being performed by an AR headset, it is understood that these actions of the method 400 may alternatively be performed by another computer system or combination of computer systems.

The method 400 may include, at action 402, affixing an optical code to a patient. In some embodiments, the optical code may be perceptible to an optical sensor. In some embodiments, the affixing of the optical code to the patient may include affixing a bandage with the optical code printed thereon to an outside layer of the patient. In some embodiments, the optical code may be a linear barcode, a matrix two-dimensional (2D) barcode, a Quick Response (QR) code, or some combination thereof. For example, a medical professional or automated system may affix, at action 402, the optical code 200 (in the form of a QR code) to the patient 106 by affixing the bandage 202 to the patient with the optical code 200 printed thereon.

The method 400 may include, at action 404, affixing a pattern of markers to the patient in a fixed position relative to a position of the optical code. In some embodiments, the pattern of markers may be perceptible to a non-optical imaging modality. In some embodiments in which the optical code is printed on a bandage, the affixing of the pattern of markers to the patient in the fixed position relative to the position of the optical code may include the pattern of markers being affixed to the bandage in the fixed position relative to the position of the optical code. In these embodiments, the pattern of markers may be embedded within the bandage, such as where the pattern of markers is embedded within an ink with which the optical code is printed on the bandage and the ink includes a material that is perceptible to the non-optical imaging modality. In these embodiments, the material that is perceptible to the non-optical imaging modality may be a radio-opaque material that is not transparent to X-rays, a magnetically visible material, or a radioactive material. In some embodiments, the affixing of the optical code to the patient may include printing the optical code on skin of the patient. In some embodiments, the affixing of the optical code to the patient may include placing an article of clothing on the patient with the optical code printed thereon. For example, a medical professional or automated system may affix, at action 404, the markers 206 to the patient 106 in the pattern disclosed in FIG. 2, and in the fixed positions disclosed in FIG. 2 relative to the position of the optical code 200, by affixing the bandage 202 to the patient 106 with the optical code 200 printed thereon and the pattern of the markers 206 affixed thereto. Alternatively, the pattern of the markers 206 may be embedded directly in the ink with which the optical code 200 is printed on the bandage 202. Alternatively, the optical code 200 may be printed onto the clothing 107 and the markers 206 may be affixed to the clothing 107 that is placed on the patient 106, or the optical code 200 may be printed (at least temporarily) directly on the skin 106*a* of the patient 106 and the markers 206 may be affixed (at least temporarily) directly to the skin 106*a* of the patient 106.

The method 400 may include, at action 406, capturing image data of the patient. In some embodiments, the image data of the patient may be captured using the non-optical imaging modality to which the markers are perceptible. In some embodiments, the image data may include an inner layer of the patient as well as the pattern of markers in a fixed position relative to a position of the inner layer of the patient. In some embodiments, the image data may include two-dimensional (2D) image data, three-dimensional (3D) image data, four-dimensional (4D) image data, or some combination thereof. For example, a medical professional or automated system may employ a non-optical imaging modality to capture, at action 406, image data of the patient 106 that includes both an inner layer of the patient (such as the bones 106*b* of the patient 106) as well as the pattern of the markers 206 in a fixed position relative to the position of the bones 106*b* of the patient 106.

In some embodiments, image data for the patient 106 may be captured or generated using one or more methods, either in real-time while the patient 106 is in the environment 100 and/or prior to the patient 106 entering the environment 100. For example, some of the image data may be obtained prior to the patient 106 entering the environment 100, and then the image data may be augmented with additional image data that is obtained in real-time while the patient 106 is in the environment 100. For example, image data of the patient 106 may include, but is not limited to, Magnetic Resonance Imaging (MRI) images, Computerized Tomography (CT) scan images, X-ray images, Positron Emission Tomography (PET) images, ultrasound images, fluorescence images, Infrared Thermography (IRT) images, or Single-Photon Emission Computed Tomography (SPECT) scan image, or some combination thereof. Any of these images may be in the form of still images or video images. For example, the method 400 may employ still X-ray images of the skeletal system of the patient 106 (as illustrated in FIG. 1). In another example, the method 400 may employ video images of an ultrasound of a beating heart of the patient 106. In another example, the method 400 may be capable of toggling between a still image of the heart and a real-time video of the heart beating.

Although obtained using a variety of different methods, image data for a patient may, in some embodiments, include an outer layer of the patient and multiple inner layers of the patient. For example, the outer layer of the patient 106 may include the skin 106*a* of the patient 106 and/or the clothing 107 worn by the patient 106 in FIG. 1. In another example, the outer layer of a cadaver may be a tissue layer other than skin, such as a layer of muscle or fat, where the skin has been removed from the cadaver. The inner layers of the patient 106 may include, but are not limited to, interior bones 106*b* (as illustrated in FIG. 1), muscles, organs, or fluids of the patient 106. Image data may include a 2D image, such as an X-ray image, because when the 2D image is projected into a 3D space the 2D image has 3D significance. For example, image data for the patient 106 may include a 2D X-ray image that may be projected onto the skin 106*a* or the clothing 107 of the patient 106. Image data may also include a time element, which is sometimes referred to as four-dimensional (4D) data. The image data of the inner layer(s) of the patient may include slices, transparency views, segmented images, or annotations, for example. For example, image data may include video that includes not only 3D images, but also include 3D images changing over time. The multiple inner layers may be layers that go all the way through the patient 106, or may be layers that only go to a certain partial depth into the patient 106. For example, some forms of image data, such as 3D data derived from a millimeter wave scanner, may only be configured to reveal items stored between the outer clothing and the skin of a patient. The image data may also be a combination of various types of image data.

Between actions 406 and 408 of the method 400, a period of time may pass. During this period of time, the patient may be moved, such as from one part of a room to another, or from one room in a hospital to another room in a hospital. In some embodiments, after this move of the patient 106, care may be taken to position the patient 106 on the operating table 103 in the same relative position and/or orientation that the patient 106 was in when the image data was captured. Alternatively, when the patient 106 is positioned in a different position and/or orientation on the operating table 103 than the patient 106 was in when the image data was captured or generated, the AR headset 108 may deform the image data to match the different position and/or orientation of the patient 106.

The method 400 may include, at action 408, sensing the optical code affixed to the patient and a position of the optical code in a 3D space. In some embodiments, the optical code may be sensed with an optical sensor of an AR headset. For example, an optical sensor of the AR headset 108 may sense, at action 408, the optical code 200 affixed to the patient 106 and a position of the optical code 200 in the 3D space 102.

The method 400 may include, at action 410, accessing the image data. In some embodiments, the image data may be accessed based on the optical code. In some embodiments, the optical code may be linked to medical data of the patient such that the medical data of the patient can be accessed with the optical code. In these embodiments, the optical code may be a security credential linked to medical data of the patient such that the medical data of the patient can be accessed with the optical code without additional security credentials. For example, the AR headset 108 may access, at action 410, the image data of the patient 106 based on the optical code 200 that was sensed at action 408, with the optical code 200 functioning as a security credential linked to medical data of the patient 106, such that the medical data of the patient 106 can be accessed with only the optical code 200 and without additional security credentials.

The method 400 may include, at action 412, calculating the position of the pattern of markers in the 3D space. In some embodiments, the calculation at action 412 may be based on the sensed position of the optical code in the 3D space and the fixed position of the pattern of markers relative to the position of the optical code. For example, the AR headset 108 may calculate, at action 412, the position of the pattern of the markers 206 in the 3D space 102 based on the sensed position of the optical code 200 in the 3D space 102 and the known (e.g., previously established) fixed position of the pattern of the markers 206 relative to the sensed position of the optical code 200.

The method 400 may include, at action 414, registering the position of the inner layer of the patient in the 3D space by aligning the calculated position of the pattern of markers in the 3D space with the position of the pattern of markers in the image data. In some embodiments, the registering at action 414 may be based on the calculated position of the pattern of markers in the 3D space and the fixed position in the image data of the pattern of markers relative to the position of the inner layer of the patient. For example, the AR headset 108 may register, at action 414, the position of the bones 106b of the patient 106 in the 3D space 102 by aligning the calculated position of the pattern of the markers 206 in the 3D space 102 with the position of the pattern of the markers 206 in the image data of the patient 106 based on the calculated position of the pattern of the markers 206 in the 3D space 102 and the known (e.g., previously established) fixed position in the image data of the pattern of the markers 206 relative to the position of the bones 106b of the patient 106.

The method 400 may include, at action 416, displaying in real-time the inner layer of the patient from the image data projected onto actual views of the patient. In some embodiments, the displaying at action 416 may be performed in the AR headset based on the registering at action 414. For example, the AR headset 108 may display in real-time, at action 416, the bones 106b of the patient 106 from the image data projected onto actual views of the patient 106 based on the registering at action 414.

In some embodiment, action 416 of the method 400 may further include repeating action 406 one or more time, or continuously, and then displaying the newly-captured image data from the repeated performance(s) of action 406 along with, or overlaid on, the originally-captured image data from the original performance of action 406. For example, an imaging modality such as MRI may be employed in the original performance of the action 406, and then another imaging modality such as fluorescence may be employed during a repeated performance, or a continuous performance, of the action 406, such as during a surgery to insert a catheter into a blood vessel of the patient 106. The AR headset 108 may then display in real-time, at action 416, the originally-captured MRI images overlaid with the newly-captured fluorescence images projected onto actual views of the patient 106 based on the registering at action 414. This overlaying of originally-captured image data with newly-captured image data at action 416 may further be accomplished using additional markers. For example, a fluoroscope may have an additional marker or markers to align the fluorescence images with the MRI images, and thus a surgeon may more accurately locate the correct location in a blood vessel of the patient 106 to place the catheter, and more accurately guide insertion of the catheter internally into the patient 106 during the surgery.

In some embodiments, the method 400 may accomplish alignment of image data of the patient 106 with actual views of the patient 106 using an optical code 200 affixed to the patient 106. Further, this alignment may enable a medical professional to view a virtual interior of the patient 106 while looking at the actual patient 106 through the AR headset 108 without any time consuming, cumbersome, and inaccurate manual alignment of image data with actual views of the patient 106, as is required in conventional forms of alignment. Further, employing the same optical code 200 as was used during the capturing of the image data to automatically retrieve the image data may ensure that the image data retrieved by the AR headset matches the actual patient being viewed through the AR headset without any time consuming, cumbersome, and inaccurate manual retrieval of the image data, as is required in conventional forms of alignment.

Although the actions of the method 400 are illustrated in FIG. 4 as discrete actions, various actions may be divided into additional actions, combined into fewer actions, reordered, expanded, or eliminated, depending on the desired implementation. For example, in some embodiments, actions 408-416 may be performed without performing any of actions 402-406, or with actions 402-406 having been performed previously or by another entity than the entity performing actions 408-416. Further, in some embodiments, only actions 408-414 may be performed without performing any of actions 402-406 and 416. Also, in some embodiments, action 412 may be modified to include sensing the position of the pattern of markers in the 3D space instead of calculating the position of the pattern of markers in the 3D space, such as where the AR headset 108 is capable of sensing the markers 206 directly.

Further, it is understood that the method 400 may improve the functioning of an AR system itself and may improve the field of AR. For example, the functioning of the AR headset 108 of FIG. 1 may itself be improved by the method 400 by automatically aligning image data of the patient 106 with actual views of the patient 106 using the optical code 200 affixed to the patient 106. This automatic alignment may be performed more easily and more accurately than conventional AR systems which employ manual registration.

As indicated above, the embodiments described herein may include the use of a special purpose or general purpose computer (e.g., the processor 302 of FIG. 3) including various computer hardware or software modules, as discussed in greater detail below. Further, as indicated above, embodiments described herein may be implemented using computer-readable media (e.g., the memory 304 or file system 306 of FIG. 3) for carrying or having computer-executable instructions or data structures stored thereon.

In some embodiments, the different components and modules described herein may be implemented as objects or processes that execute on a computing system (e.g., as separate threads). While some of the methods described herein are generally described as being implemented in software (stored on and/or executed by general purpose hardware), specific hardware implementations or a combination of software and specific hardware implementations are also possible and contemplated.

In accordance with common practice, the various features illustrated in the drawings may not be drawn to scale. The illustrations presented in the present disclosure are not meant to be actual views of any particular apparatus (e.g., device, system, etc.) or method, but are merely example representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, it is understood that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the summary, detailed description, claims, or drawings, should be understood to contemplate the possibilities of including one of the terms, either of the terms, or both terms. For example, the phrase "A or B" should be understood to include the possibilities of "A" or "B" or "A and B."

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

The foregoing description, for purpose of explanation, has been described with reference to specific embodiments. However, the illustrative discussions above are not intended to be exhaustive or to limit the invention as claimed to the precise forms disclosed. Many modifications and variations are possible in view of the above teachings. The embodiments were chosen and described to explain practical applications, to thereby enable others skilled in the art to utilize the invention as claimed and various embodiments with various modifications as may be suited to the particular use contemplated.

The invention claimed is:

1. A method for aligning image data of a patient with actual views of the patient using an optical code affixed to the patient, the method comprising:
   affixing an optical code to a patient, the optical code being perceptible to an optical sensor;
   affixing a pattern of markers to the patient in a fixed position relative to a position of the optical code, the pattern of markers being perceptible to a non-optical imaging modality;
   capturing image data of the patient using the non-optical imaging modality, the image data including an inner layer of the patient, the image data further including the pattern of markers in a fixed position relative to a position of the inner layer of the patient;
   sensing, with an optical sensor of an augmented reality (AR) headset, the optical code affixed to the patient and a position of the optical code in a 3D space;
   accessing the image data, the accessing being performed by the AR headset accessing a network computer where the image data is stored;
   calculating, based on the sensed position of the optical code in the 3D space and the fixed position of the pattern of markers relative to the position of the optical code, the position of the pattern of markers in the 3D space;

registering, based on the calculated position of the pattern of markers in the 3D space and the fixed position in the image data of the pattern of markers relative to the position of the inner layer of the patient, the position of the inner layer of the patient in the 3D space by aligning the calculated position of the pattern of markers in the 3D space with the position of the pattern of markers in the image data, the registering being performed by the AR headset; and displaying in real-time, in the AR headset and based on the registering, the inner layer of the patient from the image data projected onto actual views of the patient.

2. The method as recited in claim 1, wherein the affixing of the optical code to the patient includes affixing a bandage with the optical code printed thereon to an outside layer of the patient.

3. The method as recited in claim 2, wherein the affixing of the pattern of markers to the patient in the fixed position relative to the position of the optical code includes the pattern of markers being affixed to the bandage in the fixed position relative to the position of the optical code.

4. The method as recited in claim 3, wherein the pattern of markers is embedded within the bandage.

5. The method as recited in claim 3, wherein:
the pattern of markers is embedded within an ink with which the optical code is printed on the bandage; and
the ink includes a material that is perceptible to the non-optical imaging modality.

6. The method as recited in claim 5, wherein the material that is perceptible to the non-optical imaging modality is a radio-opaque material that is not transparent to X-rays, a magnetically visible material, or a radioactive material.

7. The method as recited in claim 1, wherein the non-optical imaging modality includes a Magnetic Resonance Imaging (MRI) modality, a Computerized Tomography (CT) scan modality, an X-ray modality, a Positron Emission Tomography (PET) modality, an ultrasound modality, a fluorescence modality, an Infrared Thermography (IRT) modality, or a Single-Photon Emission Computed Tomography (SPECT) scan modality.

8. The method as recited in claim 1, wherein the image data includes two-dimensional (2D) image data, three-dimensional (3D) image data, four-dimensional (4D) image data, or some combination thereof.

9. The method as recited in claim 1, wherein the optical code is a linear barcode, a matrix two-dimensional (2D) barcode, a Quick Response (QR) code, or some combination thereof.

10. The method as recited in claim 1, wherein the optical code is linked to medical data of the patient such that the medical data of the patient can be accessed with the optical code.

11. The method as recited in claim 1, wherein
the optical code is a security credential linked to medical data of the patient such that the medical data of the patient is accessed with the optical code without additional security credentials.

12. The method as recited in claim 11, wherein the affixing of the optical code to the patient includes printing the optical code on skin of the patient.

13. The method as recited in claim 11, wherein the affixing of the optical code to the patient includes placing an article of clothing on the patient with the optical code printed thereon.

14. The method as recited in claim 2, wherein the bandage is formed from a material that is sterilizable.

15. A method for aligning image data of a patient with actual views of the patient using an optical code affixed to the patient, the method comprising:

affixing a bandage to a patient, the bandage including an optical code printed thereon and a pattern of markers affixed thereto, the pattern of markers having a fixed position in the bandage relative to a position of the optical code on the bandage, the optical code being perceptible to an optical sensor, the pattern of markers being perceptible to a non-optical imaging modality;

capturing image data of the patient using the non-optical imaging modality, the image data including an inner layer of the patient, the image data further including the pattern of markers in a fixed position relative to a position of the inner layer of the patient;

sensing, with an optical sensor of an augmented reality (AR) headset, the optical code affixed to the patient and a position of the optical code in a 3D space;

accessing the image data, the accessing being performed by the AR headset accessing a network computer where the image data is stored;

calculating, based on the sensed position of the optical code in the 3D space and the fixed position of the pattern of markers relative in the bandage to the position of the optical code on the bandage, the position of the pattern of markers in the 3D space;

registering, based on the calculated position of the pattern of markers in the 3D space and the fixed position in the image data of the pattern of markers relative to the position of the inner layer of the patient, the position of the inner layer of the patient in the 3D space by aligning the calculated position of the pattern of markers in the 3D space with the position of the pattern of markers in the image data, the registering being performed by the AR headset; and displaying in real-time, in the AR headset and based on the registering, the inner layer of the patient from the image data projected onto actual views of the patient.

16. The method as recited in claim 15, wherein:
the pattern of markers is embedded within an ink with which the optical code is printed on the bandage; and
the ink includes a radio-opaque material that is not transparent to X-rays, a magnetically visible material, or a radioactive material.

17. The method as recited in claim 15, wherein the optical code is a security credential linked to medical data of the patient such that the medical data of the patient can be accessed with the optical code without additional security credentials.

* * * * *